United States Patent
Lee et al.

(10) Patent No.: US 9,567,349 B2
(45) Date of Patent: Feb. 14, 2017

(54) PREPARING METHOD OF AG NANO-PARTICLE AND HYDROPHOBIC SPHERICAL AG NANO-PARTICLE PREPARED USING THE SAME

(71) Applicant: Korea Basic Science Institute, Daejeon (KR)

(72) Inventors: Gaehang Lee, Daejoen (KR); Yeon Suk Choi, Daejeon (KR); Doo Ri Bae, Daejeon (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 353 days.

(21) Appl. No.: 14/176,357

(22) Filed: Feb. 10, 2014

(65) Prior Publication Data

US 2015/0132595 A1 May 14, 2015

(30) Foreign Application Priority Data

Nov. 8, 2013 (KR) ........................ 10-2013-0135157

(51) Int. Cl.
  *B22F 1/00* (2006.01)
  *B22F 9/24* (2006.01)
  *C07F 1/10* (2006.01)

(52) U.S. Cl.
  CPC ............... *C07F 1/10* (2013.01); *B22F 1/0044* (2013.01); *B22F 1/0048* (2013.01); *B22F 9/24* (2013.01); *Y10T 428/12* (2015.01)

(58) Field of Classification Search
  CPC ......... B22F 1/0048; B22F 1/0044; B22F 9/24; B22F 2301/255; B22F 2304/05
  See application file for complete search history.

(56) References Cited

U.S. PATENT DOCUMENTS 8,211,205 B1 * 7/2012 Didenko ............... B22F 9/24
  75/371
2011/0143051 A1 * 6/2011 Ohashi ............... C09D 11/0235
  427/553

(Continued)

FOREIGN PATENT DOCUMENTS

KR 1020080027681 3/2008
KR 1020090061016 6/2009

(Continued)

OTHER PUBLICATIONS

Derwent Acc No. 2011-N05269 for the patent family including WO 2011129562 A2 by Hyeon et al published Oct. 20, 2011. Abstract.*

(Continued)

*Primary Examiner* — George Wyszomierski
*Assistant Examiner* — Tima M McGuthry Banks
(74) *Attorney, Agent, or Firm* — Sughrue Mion, PLLC (57) ABSTRACT

Provided is a preparing method of an Ag nano-particle for mass-producing Ag nano-particles, the method including: performing a first reaction of a reaction solution containing an Ag precursor and oleylamine at a set first temperature $T_1$; performing a second reaction of the reaction solution at a second temperature $T_2$ set so as to be higher than the first temperature; and obtaining a reactant from the reaction solution, wherein at least one of the first and second reactions is performed in a state in which the reaction solution is not stirred.

9 Claims, 7 Drawing Sheets (56) References Cited

U.S. PATENT DOCUMENTS

| | | | | |
|---|---|---|---|---|
| 2012/0060649 A1* | 3/2012 | Malekzadeh | ............. | B22F 9/08 |
| | | | | 75/336 |
| 2012/0240728 A1* | 9/2012 | Gann | ........................ | B22F 9/24 |
| | | | | 75/370 |
| 2013/0133484 A1* | 5/2013 | Hyeon | ..................... | C01G 5/00 |
| | | | | 75/362 |

FOREIGN PATENT DOCUMENTS

| | | | | |
|---|---|---|---|---|
| KR | 1020110113877 | | 10/2011 | |
| KR | 10-2003-0018536 A | | 2/2013 | |
| WO | WO 2011112608 A1 * | | 9/2011 | ............ B22F 1/0018 |
| WO | WO 2011129562 A2 * | | 10/2011 | |

OTHER PUBLICATIONS

"Oleylamine." Sigma-Aldrich. Sigma-Aldrich Co. LLC, 2012. Web. Mar. 15, 2016.*
"Oleic Acid." Oleic Acid. Sigma-Aldrich, 2016. Web. Mar. 15, 2016.*
Hyeon et al. WO 2011129562 A2 published Oct. 20, 2011. Machine translation.*
The Korean Intellectual Property Office, Office Action dated Nov. 28, 2014 , issued in the Korean Patent Application No. 10-2013-0135157.

* cited by examiner

PREPARING METHOD OF AG NANO-PARTICLE AND HYDROPHOBIC SPHERICAL AG NANO-PARTICLE PREPARED USING THE SAME

CROSS-REFERENCE TO RELATED APPLICATIONS

This application claims priority under 35 U.S.C. §119 to Korean Patent Application No. 2013-0135157, filed on Nov. 8, 2013, in the Korean Intellectual Property Office, the disclosure of which is incorporated herein by reference in its entirety.

TECHNICAL FIELD

The following disclosure relates to a preparing method of an Ag nano-particle, and more particularly, to a preparing method of an Ag nano-particle capable of mass-producing the Ag nano-particle having excellent quality and uniformity through a simplified process, and a hydrophobic spherical Ag nano-particle prepared using the same.

BACKGROUND

A silver (Ag) metal has optical properties sensitive to a size and shape thereof, and indicates high plasmon excitation efficiency, high electric conductivity, and high thermal conductivity. It was found that an Ag nano-particle using these properties is a prominent material in a field such as an organic catalyst field, an optical sensor field, an electronic printing field, a photonics field, and the like.

Since a size and shape of this Ag nano-particle have a large influence on optical, electrical, and surface energy properties, it is important to synthesize significantly uniform Ag nano-particle. In order to synthesize the Ag nano-particle by a bottom-up method, basically, an experimental environment capable of reducing $Ag^+$ ions in a solution containing the $Ag^+$ ions should be prepared.

Introducing synthesizing methods of an Ag nano-particle, a method of transferring UV/vis energy, microwave energy, or ultrasound energy to a solution via radiation to reduce $Ag^+$ ions, a method of adding a strong reducing agent such as borohydride based reducing agents, hydrazine, or the like, at room temperature, and a method of adding a weak reducing agent such as sodium citrate, ascorbic acid, or polyol in a state in which a solution is heated, have been known.

Among the methods as described above, in the energy radiation method, a synthetic method is significantly simple, but it is impossible to apply uniform energy to the entire reaction solution, such that non-uniform particles are generated. In addition, in the method of adding an arbitrary reducing agent, since various chemical species such as a surfactant, a solvent, a reducing agent in addition to an Ag precursor are added, synthetic cost is increased, such that this method is not suitable for mass-production.

Therefore, in a preparing method for mass-producing an Ag nano-particle in an industrial field, the chemical species should be minimally required in synthesis, the cost should be cheap, an amount of energy applied thereto should be small, and the Ag nano-particle should be prepared through a simple processing step.

RELATED ART DOCUMENT

Patent Document

Korean Patent Laid-Open Publication No. 2013-0018536

SUMMARY

An embodiment of the present invention is directed to providing a preparing method of an Ag nano-particle capable of mass-producing Ag nano-particles having excellent quality and uniformity by a simplified process at the time of preparing the Ag nano-particle. At the same time, an object of the present invention is to provide a preparing method of an Ag nano-particle capable of decreasing a cost by using relatively cheap chemical species to prepare Ag nano-particles.

In addition, an embodiment of the present invention is directed to providing hydrophobic spherical Ag nano-particles prepared by the preparing method to thereby have excellent quality and uniformity.

In one general aspect, a preparing method of an Ag nano-particle, the preparing method includes: performing a first reaction of a reaction solution containing an Ag precursor and oleylamine at a set first temperature $T_1$; performing a second reaction of the reaction solution at a second temperature $T_2$ set so as to be higher than the first temperature; and obtaining a reactant from the reaction solution, wherein at least one of the first and second reactions is performed in a state in which the reaction solution is not stirred.

The preparing method may further include, after the performing of the second reaction, cooling the reaction solution to room temperature.

Each of the first and second reactions may be performed in the atmosphere (air).

The reaction solution may further contain oleic acid.

The reaction solution may be composed of the Ag precursor, oleylamine, and oleic acid.

The reaction solution may not further contain a reducing agent, a dispersant, a surfactant, and a solvent except for oleylamine and oleic acid.

The Ag precursor may be silver nitrate ($AgNO_3$).

The reaction solution may contain 10 to 20 wt % of the Ag precursor.

In the performing of the first reaction, the first reaction may be performed by stirring the reaction solution at 80 to 110° C. for 10 to 120 minutes.

In the performing of the second reaction, the second reaction may be performed at 120 to 150° C. for 1 hour or more without stirring the reaction solution.

The obtaining of the reactant may be performed by centrifugation of the reaction solution.

In the obtaining of the reactant, a purity of the reactant in the reaction solution may be increased by repeatedly performing the centrifugation two times or more.

In another general aspect, a hydrophobic spherical Ag nano-particle may be prepared by the preparing method as described above.

DETAILED DESCRIPTION OF EMBODIMENTS

Hereinafter, a preparing method of an Ag nano-particle according to the present invention and an Ag nano-particle prepared using the same will be described in detail with reference to the accompanying drawings. The drawings to be provided below are provided by way of example so that the idea of the present invention can be sufficiently transported to those skilled in the art. Therefore, the present invention is not limited to the drawings to be provided below, but may be modified in many different forms. In addition, the drawings to be provided below may be exaggerated in order to clarify the scope of the present invention. Here, technical terms and scientific terms used in the present specification have the general meaning understood by those skilled in the art to which the present invention pertains unless otherwise defined, and a description for the known function and configuration obscuring the present invention will be omitted in the following description and the accompanying drawings.

Figure 1:
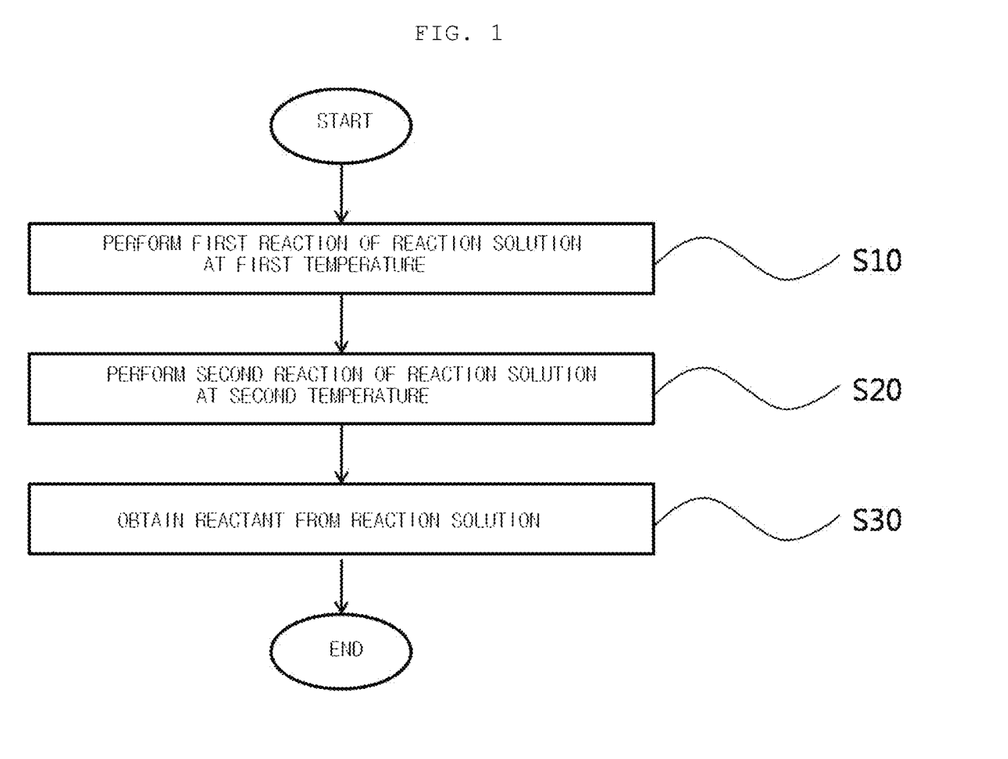
FIG. 1 is a process flow chart schematically showing a preparing method of an Ag nano-particle according to an exemplary embodiment of the present invention.

The preparing method of an Ag nano-particle according to the present invention includes: performing a first reaction of a reaction solution containing an Ag precursor and oleylamine at a set first temperature $T_1$ (S10); performing a second reaction of the reaction solution at a second temperature $T_2$ set so as to be higher than the first temperature (S20); and obtaining a reactant from the reaction solution (S30) as shown in FIG. 1. In addition, the preparing method may further include, after the performing of the second reaction (S20), cooling the reaction solution to room temperature, and at least one of the first and second reactions may be performed without stirring.

In addition, in the preparing method of an Ag nano-particle according to the present invention, each of the first and second reactions may be performed in the atmosphere (air).

More specifically, in the preparing method of an Ag nano-particle according to the present invention, firstly, the reaction solution containing the Ag precursor and oleylamine is prepared in the performing of the first reaction (S10).

Here, the Ag precursor is not particularly limited as long as it smoothly reacts with oleylamine, which is another component of the reaction solution, to thereby be suitable for preparing the Ag nano-particle, but in view of securing quality and uniformity of the prepared Ag nano-particle, it is preferable that the Ag precursor is silver nitrate ($AgNO_3$).

In this case, the reaction solution may contain 10 to 20 wt % of the Ag precursor. In detail, in the case in which a content of the Ag precursor in the reaction solution is less than 10 wt %, the content of the Ag precursor in the reaction solution is insignificant, such that a size of the prepared Ag nano-particle is not adjusted. That is, even though the content of the Ag precursor in the reaction solution is less than 10 wt %, the size of the prepared Ag nano-particle is not further decreased. On the contrary, in the case in which the content of the Ag precursor in the reaction solution is more than 20 wt %, the Ag precursor is not completely dissolved in a solvent in the performing of the first reaction, which makes the reaction solution to be in a non-uniform state, such that an Ag nano-particle of which a shape and size are non-uniform may be synthesized during a process of forming the Ag nano-particle in the performing of the second reaction. The content of the Ag precursor in the entire reaction solution is excessive, the entire Ag precursor does not participate in a reduction reaction with oleylamine, but agglomeration of the Ag precursor may be generated, or the Ag precursor may remain in the reaction solution after the reduction reaction with oleylamine.

Provided that the content of the Ag precursor in the reaction solution is in a range of 10 to 20 wt %, since, as the content of the Ag precursor increases, a content of oleylamine relatively decreases, stability of an Ag precursor-oleylamine complex is deteriorated, which increases a thermal decomposition rate of the Ag precursor and promotes reduction of an Ag precursor cation by oleylamine, such that the size of the prepared Ag nano-particle may become fine.

In addition, oleylamine may serve as a solvent for dissolving the Ag precursor in the reaction solution, a reducing agent for the reduction reaction, and a surfactant for improving dispersion of the Ag precursor. In this case, oleic acid may be further contained in the reaction solution of the present invention, and oleic acid added as described above may affect a reaction rate of the Ag precursor and oleylamine to thereby adjust the size of the prepared Ag nano-particle in addition to serving as the solvent and the surfactant together with oleylamine.

As described above, oleic acid added to the reaction solution inhibits the binding between the Ag precursor and oleylamine to make a state of the Ag precursor-oleylamine complex to be unstable, such that oleic acid may increase the thermal decomposition rate of the Ag precursor and promote the reduction reaction by oleylamine. In addition, when a rate of the reduction reaction is increased as described above, an Ag nano-particle having a fine size may be prepared due to rapid and highly dense nucleation of the reduced Ag nano-particle. In this case, an addition amount of oleic acid is not particularly limited, and a significantly small amount of oleic acid may serve to increase the thermal decomposition rate of the Ag precursor and promote the reduction reaction by oleylamine.

In this case, a content of oleic acid is not particularly limited as described above, but as a specific example, 0.05 to 2 parts by volume of oleic acid may be added based on 100 parts by volume of oleylamine, which is the solvent. However, a trace amount of oleic acid may increase the thermal decomposition rate of the Ag precursor as described above, even in the case of a large amount of oleic acid, oleic acid does not have a large influence on the reaction, such that the present invention is not limited by the addition amount of oleic acid based on oleylamine.

Therefore, a dispersion solution of the present invention may be composed of the Ag precursor, oleylamine, and oleic acid. That is, the dispersion solution of the present invention is characterized in that a solvent, a reducing agent, or a surfactant except for oleylamine is not additionally contained therein, and accordingly, the Ag nano-particle which excellent quality and uniformity are secured as compared to an Ag nano-particle according to the related art may be prepared.

Then, the first reaction of the reaction solution prepared as described above is performed at the set first temperature $T_1$.

More specifically, in the performing of the first reaction, which is a reaction process step of mainly performing thermal decomposition of the Ag precursor, the reaction solution may be stirred at 80 to 110° C. for thermal decomposition of the Ag precursor. At this time, the first reaction may be performed for 10 to 120 minutes. More preferably, thermal decomposition efficiency of the Ag precursor in the reaction solution may be increased by stirring the reaction solution at 100 to 110° C. for 30 to 120 minutes.

In this time, when a reaction temperature is less than 80° C. or a reaction time is less than 10 minutes, thermal decomposition of the Ag precursor may not be smoothly performed. Further, when the reaction temperature is more than 110° C. or the reaction time is more than 120 minutes, after thermal decomposition of the Ag precursor, a reduction reaction of the thermally decomposed Ag precursor and oleylamine may be generated. At this time, non-uniform Ag nano-particles may be generated by stirring performed during the first reaction.

In order to suppress generation of the non-uniform Ag nano-particle, the present invention is characterized in that the Ag precursor-oleylamine complex is formed by the reduction reaction in the performing of the second reaction separately from the thermal decomposition reaction of the Ag precursor. At this time, the performing of the second reaction is characterized in that the second reaction is performed without stirring so that an Ag nano-particle having an excellent hydrophobic property and spherical shape and a uniform size is formed.

Therefore, the second reaction of the reaction solution subjected to the first reaction is performed at the set second temperature $T_2$ (S20).

In detail, the performing of the second reaction is a reaction process step of forming the Ag nano-particles (that is, the Ag precursor-oleylamine complex) by reduction reaction between the Ag precursor of which the thermal decomposition is carried out and the oleylamine in the reaction solution. In this case, the reduction reaction rate is slightly adjusted according to the content of the Ag precursor in the reaction solution or presence or absence of added oleic acid, and when the reduction reaction is increased, fine Ag nano-particles may be well formed, and when the reduction reaction rate is relatively decreased, Ag nano-particles having a relatively large size may be formed.

In more detail, in the performing of the second reaction, the second reaction may be performed at a temperature higher than the temperature $T_1$ at the time of the first reaction for thermal decomposition of the Ag precursor. In this case, it may be preferable that the second reaction is performed at 120 to 150° C. without stirring and the second reaction is performed for 1 hour or more so that the reduction reaction is sufficiently performed. More preferably, when the second reaction is performed for 5 hours or more, the reduction reaction of the Ag precursor and oleylamine may be sufficiently secured.

In the case in which the second reaction as described above is performed at a temperature less than 120° C. or performed for a time less than 1 hour, the reduction reaction of the Ag precursor and oleylamine may not be smoothly performed. In addition, when the second reaction is performed at a temperature higher than 150° C. or performed in a stirring state, the reduction reaction of the Ag precursor and oleylamine may be excessively performed, such that non-uniform Ag nano-particles may be generated.

When generation of the Ag nano-particle is completed according to the above-mentioned process, the reaction solution may be cooled to room temperature. At this time, the reaction solution may be naturally cooled by being left at room temperature or by using an artificial method in a range in which the cooling is not rapidly performed. In this case, in view of an advantage for inhibiting agglomeration of the Ag nano-particle by rapid cooling, it is preferable that the cooling is performed in a range in which a cooling rate does not exceed 10° C./min.

Finally, the Ag nano-particle dispersed in the reaction solution as the reactant is obtained (S30).

An obtaining method of the Ag nano-particle is not particularly limited, but it is preferable in view of increasing a yield that the Ag nano-particle is obtained by centrifugation. When the centrifugation is performed as described above, the reaction solution is separated into a supernatant containing the reactant and a lower layer solution containing impurities except for the reactant, reaction residues, and the like, by gravity, and among them, only the supernatant may be obtained by removing the lower layer solution using a separate separator, or the like.

The centrifugation as described above may be repeatedly performed at least two times, such that purity of the supernatant containing the reactant may be increased.

The Ag nano-particle prepared by the above-mentioned method may be formed in a spherical shape, and a surface of the Ag nano-particle is coated with oleylamine, such that the Ag nano-particle may have a hydrophobic property. Further, in the preparing method of an Ag nano-particle according to the present invention, Ag nano-particles having a uniform size of 2 to 10 nm may be prepared.

Hereinafter, specific Examples and Experimental Examples of the preparing method of an Ag nano-particle according to the present invention, and the Ag nano-particles will be provided. However, these specific Examples and Experimental Examples are provided in order to experimentally verify excellence of the present invention, and the present invention is not limited thereto.

Example 1

After 1 g of $AgNO_3$ and 10 mL of oleylamine were put into a 50 mL vial, the mixture was heated to 100° C., and a stirring state was maintained for 1 hour. After stopping the stirring, the mixture is left at 130° C. for 7 hours. Then, the reaction solution was cooled to room temperature. 10 mL of ethanol was added to the reaction solution of which a temperature became room temperature, and centrifugation was performed at 3,000 rpm for 10 minutes, thereby obtaining precipitates. In order to remove reaction by-products and excess oleylamine, 5 mL of toluene and 10 mL of ethanol were added to the precipitates, and centrifugation was performed at 3,000 rpm for 10 minutes, thereby obtaining precipitates.

Example 2

An experimental process was the same as that in Example 1 except for using 2 g of $AgNO_3$ instead of 1 g of $AgNO_3$.

Example 3

An experimental process was the same as that in Example 1 except for using 9 mL of oleylamine and 1 mL of oleic acid instead of 10 mL of oleylamine.

Example 4

An experimental process was the same as that in Example 1 except for using 0.5 g of AgNO$_3$ instead of 1 g of AgNO$_3$.

Example 5

An experimental process was the same as that in Example 1 except for using 9.5 mL of oleylamine and 0.5 mL of oleic acid instead of 10 mL of oleylamine.

Example 6

An experimental process was the same as that in Example 1 except for using 9.9 mL of oleylamine and 0.1 mL of oleic acid instead of 10 mL of oleylamine.

Comparative Example 1

After 1 g of AgNO$_3$ and 10 mL of oleylamine were put into a 50 mL vial, the mixture was heated to 100° C. for 1 hour and then heated at 130° C. for 5 hours. A stirring state of the solution was maintained in all of the heating reactions.

Comparative Example 2

After 1 g of AgNO$_3$ and 5 mL of oleylamine were put into a 50 mL vial, the mixture was heated to 100° C. for 1 hour and then heated at 150° C. for 5 hours. A stirring state of the solution was maintained in all of the heating reactions.

Comparative Example 3

After 1 g of AgNO$_3$ and 10 mL of oleylamine were put into a 50 mL vial, the mixture was heated to 100° C. for 1 hour, and 0.1 g of NaBH$_4$ was added thereto. A stirring state of the solution was maintained in all of the heating reactions. A centrifugation process was the same as in Example 1.

Experimental Example 1

Figure 2:
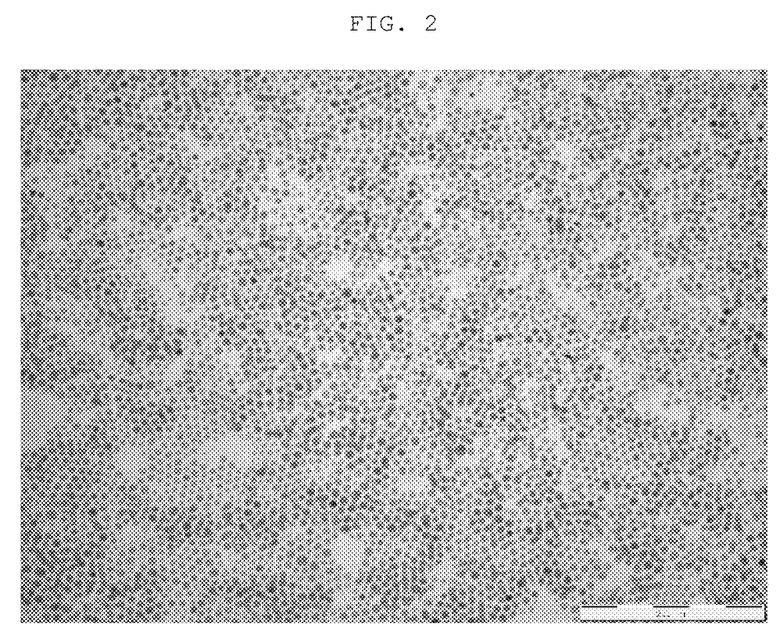
FIGS. 2 to 4 are transmission electronic microscope images of Ag nano-particles prepared in Examples 1 to 3 according to the present invention.
Figure 3:
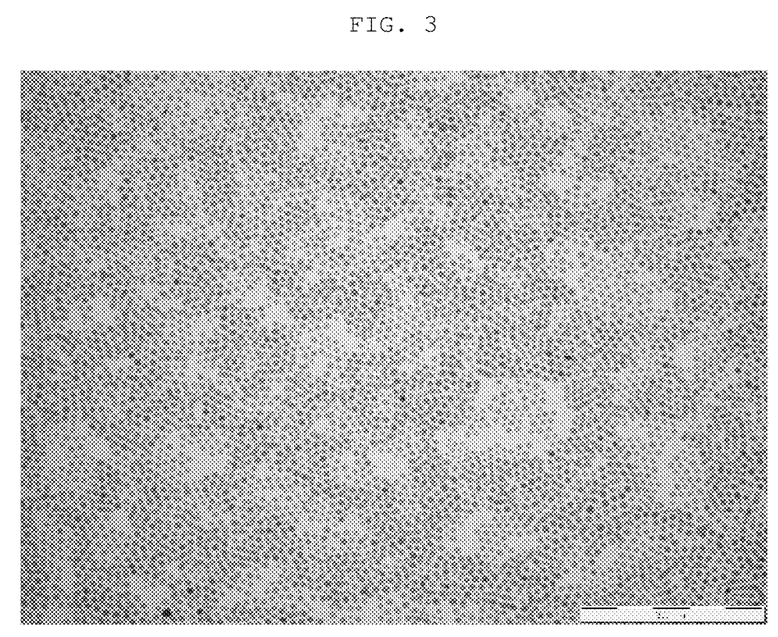
Figure 4:
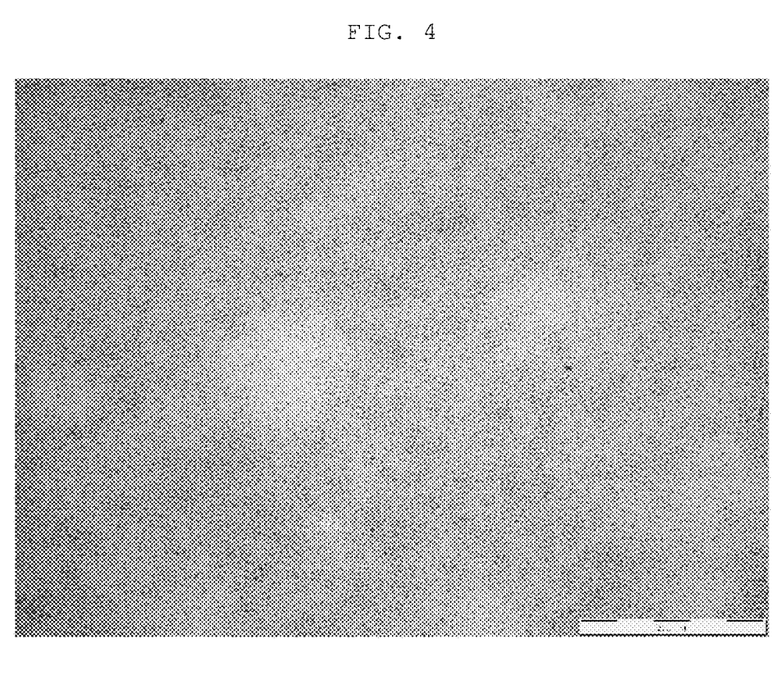

FIGS. 2 to 4 are transmission electronic microscope images of Ag nano-particles prepared in Examples 1 to 3 of the present invention. Referring to FIGS. 2 to 4, it may be confirmed by microscopic observation that the Ag nano-particle prepared by the preparing method of an Ag nano-particle according to the present invention had a spherical shape.

In detail, FIGS. 2, 3, and 4 are transmission electronic microscope images of Ag nano-particles prepared in Examples 1, 2, and 3, respectively. It may be confirmed that an average particle size of the Ag nano-particles of Example 1 was 10.5±0.9 nm, an average particle size of the Ag nano-particles of Example 2 was 5.3±0.4 nm, and an average particle size of the Ag nano-particles of Example 3 was 2.5±0.2 nm.

In addition, comparing the results of Examples 1 and 2, it may be confirmed that when the content of AgNO$_3$ was increased, the size of the prepared Ag nano-particle was decreased, and comparing the results of Examples 1 and 3, it may be confirmed that when oleic acid was added, the size of the prepared Ag nano-particle was decreased.

Experimental Example 2

Figure 5:
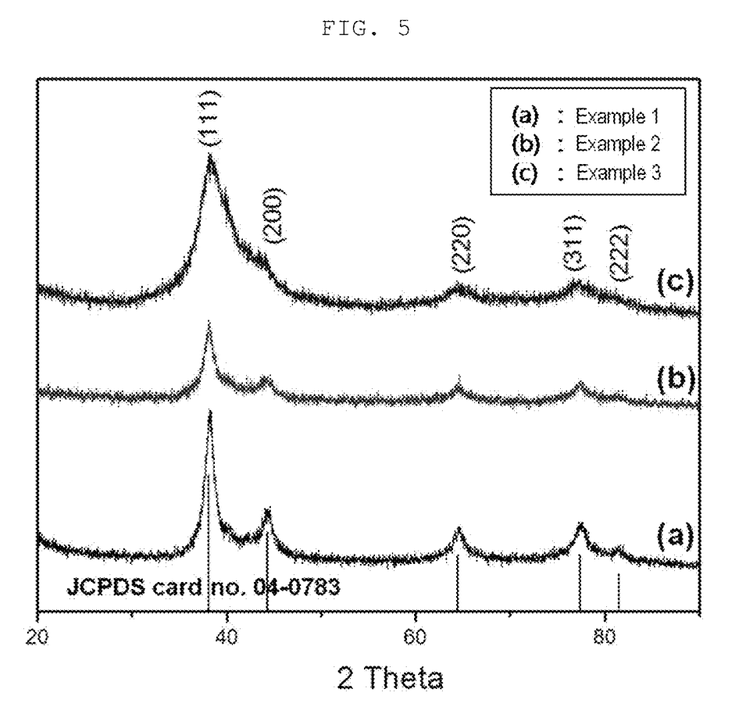
FIG. 5 is X-ray diffraction (XRD) patterns of the Ag nano-particles prepared in Examples 1 to 3 of the present invention.

FIG. 5 is an analysis result of X-ray diffraction (XRD) patterns of the Ag nano-particles prepared in Examples 1 to 3 of the present invention. Referring to an XRD pattern of each of the nano-particles of Example 1 (a; black line), Example 2 (b; red line), and Example 3 (c; blue line), it may be confirmed that the XRD patterns of the nano-particles of Examples 1 to 3 were the same as that of a reference material of silver, 'JCPDS Card No. 56-0269'. Therefore, it may be confirmed that the Ag nano-particle prepared according to the present invention had a face-centered cubic crystalline structure.

In addition, peaks of the XRD pattern became broad in a sequence of Example 1, Example 2, and Example 3, which may be interpreted that the size of the prepared Ag nano-particle was decreased.

Experimental Example 3

Figure 6:
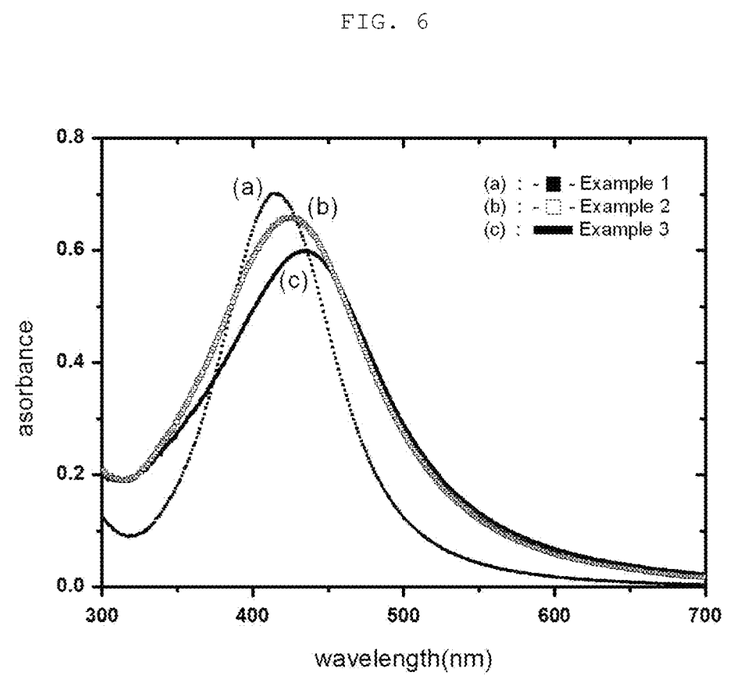
FIG. 6 is a UV/Vis spectra of the Ag nano-particles prepared in Examples 1 to 3 of the present invention.

FIG. 6 is a UV/Vis spectra of the Ag nano-particles prepared in Examples 1 to 3 according to the present invention. Referring to FIG. 6, it may be confirmed that the Ag nano-particles of Example 1, Example 2, and Example 3 absorbed light at 435.3 nm, 426.7 nm, and 415.8 nm, respectively. In the UV/Vis spectra as described above, the smaller the size of the nano-particle, the shorter the wavelength at which the light was absorbed. Therefore, comparing the results of Examples 1 and 2 with each other, it may be confirmed that as the content of AgNO$_3$ was increased, the size of the prepared Ag nano-particle was decreased, and comparing the results of Examples 1 and 3 with each other, it may be confirmed that in the case of adding oleic acid, the size of the prepared Ag nano-particle was decreased.

Experimental Example 4

Figure 7:
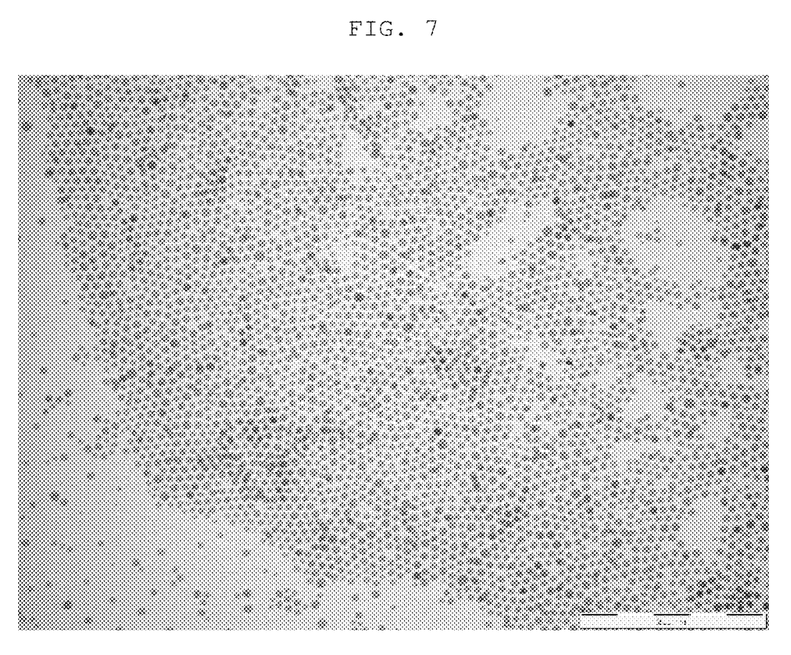
FIGS. 7 to 9 are transmission electronic microscope images of Ag nano-particles prepared in Examples 4 to 6 of the present invention.
Figure 8:
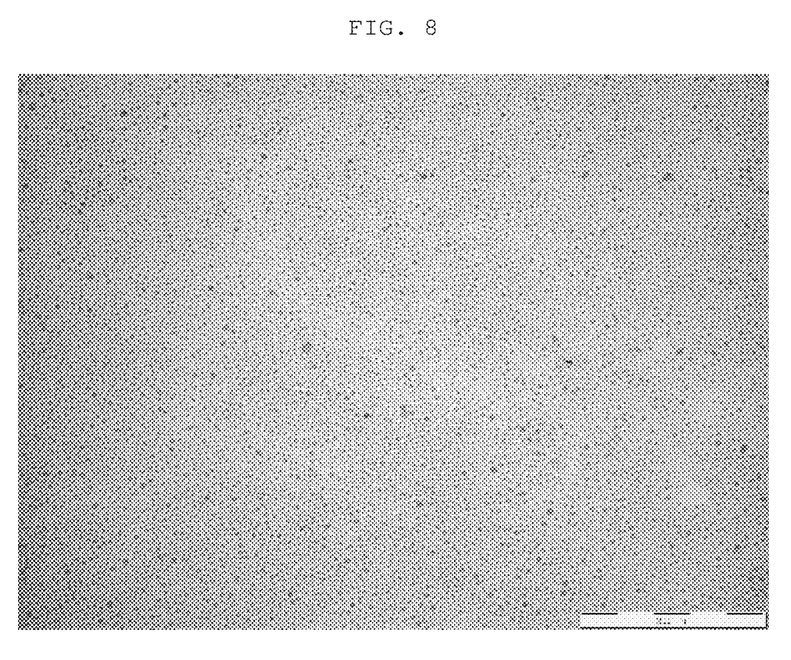
Figure 9:
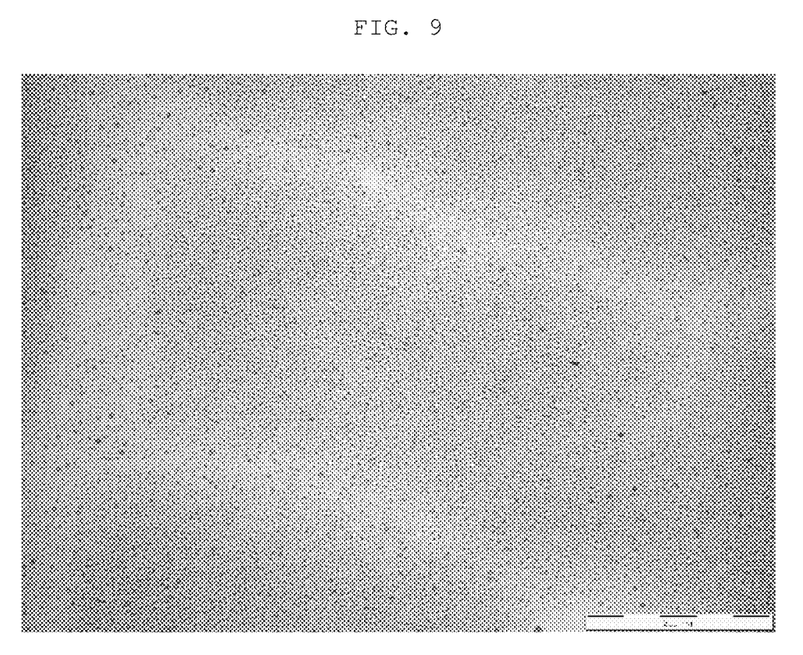

FIGS. 7 to 9 are transmission electronic microscope images of Ag nano-particles prepared in Examples 4 to 6 according to the present invention. Referring to FIGS. 7 to 9, it may be confirmed that an average particle size of the Ag nano-particles of Example 4 was 10.3±0.9 nm, an average particle size of the Ag nano-particles of Example 5 was 2.5±0.2 nm, and an average particle size of the Ag nano-particles of Example 6 was 2.5±0.2 nm.

Here, comparing the result of the transmission electronic microscope image of Example 4 in FIG. 7 with that of Example 1 in FIG. 2, it may be confirmed that when in the present invention, the content of the Ag precursor was less than 10 wt %, the size of the prepared Ag nano-particle was not increased nor decreased, and was almost equal to the size of the Ag nano-particle prepared in Example 1. That is, it may be confirmed that in the case in which the content of the Ag precursor is less than a predetermined content (10 wt %), the size of the prepared Ag nano-particle was not affected by the content of the Ag precursor.

In addition, comparing the results of the transmission electronic microscope images of Example 5 in FIG. 8 and Example 6 in FIG. 9 with that of Example 3 in FIG. 4, it may be confirmed that even in the case in which addition amounts (0.5 mL and 0.1 mL) of oleic acid in Examples 5 and 6 were smaller than the addition amount (1 mL) of oleic acid in Example 3, the sizes of the prepared Ag nano-particles were almost equal to each other. That is, it may be appreciated that the addition amount of oleic acid was not particularly limited, and even in the case of a trace amount of oleic acid, the size of the prepared Ag nano-particle may be decreased from 10.5 nm to about 2.5 nm.

Experimental Example 5

In the present invention, as an important factor for adjusting the size of the prepared Ag nano-particle at the time of preparing the Ag nano-particle, there is a control of physical force applied at the time of forming the Ag nano-particle, that is, a control of the stirring.

As shown in Examples 1 to 3, a feature of the present invention is that the reaction was primarily performed in the stirring state at 100° C. and then, secondarily performed at 130° C. without stirring, thereby preparing the Ag nano-particle.

On the contrary, in Comparative Example 1, the secondary reaction was performed in the stirring state at 130° C., and in Comparative Example 2, the secondary reaction was performed in the stirring state at 150° C. In this case, in Comparative Examples 1 and 2, a color of the reaction solution was maintained in a transparent state after the reaction was completed, such that it may be confirmed that the Ag nano-particle was not prepared after the reaction.

Therefore, it may be appreciated that when the stirring was continuously performed during the reaction, the Ag nano-particle was not prepared.

Experimental Example 6

Figure 10:
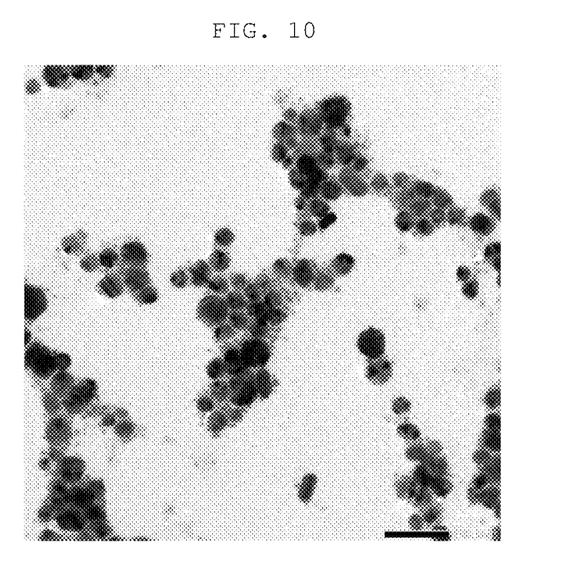
FIG. 10 is a transmission electronic microscope image of Ag nano-particles prepared in Comparative Example 3 of the present invention.

FIG. 10 is a transmission electronic microscope image of Ag nano-particles prepared in Comparative Example 3.

Another feature of the preparing method of an Ag nano-particle of the present invention is that the uniform Ag nano-particle having excellent quality may be prepared without adding another reducing agent except for oleylamine.

On the contrary, in Comparative Example 3, $NaBH_4$ was added as a reducing agent generally used in a process of synthesizing nano-particle, thereby preparing the Ag nano-particle. In this case, a color of the reaction solution was rapidly changed into a dark brown color according to the addition of the reducing agent, such that it may be confirmed that the Ag precursor was reduced to thereby form Ag nano-particle.

However, as a result of obtaining the Ag nano-particles formed in Comparative Example 3 to observe the transmission electronic microscope image thereof, it may be confirmed that Ag nano-particles having a significantly non-uniform size in a range of 50 to 10 nm were formed and mixed as shown in FIG. 10. The reason may be interpreted that a separate reducing agent was additionally added, such that the reduction rate of the Ag precursor and a growth rate of the Ag nano-particle were not smoothly controlled, thereby forming the non-uniform Ag nano-particles. Therefore, it may be confirmed that in the preparing method of an Ag nano-particle according to the present invention, there is no need to add a separate reducing agent.

With the preparing method of an Ag nano-particle according to the present invention, the Ag nano-particle having excellent quality and uniformity may be mass-produced by the simplified process. At the same time, with the preparing method of an Ag nano-particle according to the present invention, the preparing cost of the Ag nano-particle may be decreased by preparing the Ag nano-particle using the relative cheap chemical species.

In addition, with the preparing method of an Ag nano-particle according to the present invention, the hydrophobic spherical Ag nano-particle having excellent quality and uniformity may be prepared.

Hereinabove, although the present invention is described by specific matters, exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described embodiments, and the following claims as well as all modified equally or equivalently to the claims are intended to fall within the scope and spirit of the invention.

What is claimed is:

1. A method of preparing a spherical Ag nano-particle, the preparing method comprising:
   (a) performing a first reaction of a reaction solution containing an Ag precursor and oleylamine by stirring the reaction solution at 80 to 110° C. for 10 to 120 minutes in an air atmosphere;
   (b) performing a second reaction of the reaction solution at 120 to 150° C. for 1 hour or more without stirring the reaction solution in an air atmosphere;
   (c) cooling the reaction solution obtained in step (b) to room temperature after the performing of the second reaction; and
   (d) obtaining the spherical Ag nano-particle from the cooled reaction solution of step (c) by repeatedly performing centrifugation of the cooled reaction solution two times or more.

2. The method of claim 1, wherein the reaction solution of step (a) further contains oleic acid.

3. The method of claim 2, wherein the reaction solution of step (a) is composed of the Ag precursor, oleylamine, and oleic acid.

4. The method of claim 2, wherein the reaction solution of step (a) does not further contain a reducing agent, a dispersant, a surfactant, and a solvent except for oleylamine and oleic acid.

5. The method of claim 1, wherein the Ag precursor is silver nitrate.

6. The method of claim 1, wherein the reaction solution of step (a) contains 10 to 20 wt % of the Ag precursor.

7. The method of claim 1, wherein in step (d), a purity of the spherical Ag nano-particle in the reaction solution is increased by increasing the number of the centrifugation.

8. A method of preparing a spherical Ag nano-particle, the method comprising:
   performing a first reaction of a reaction solution containing a silver nitrate and oleylamine at a set first temperature $T_1$ in an air atmosphere;
   performing a second reaction of the reaction solution at a second temperature $T_2$ set so as to be higher than the first temperature in an air atmosphere;
   cooling the reaction solution to room temperature after the performing of the second reaction; and
   obtaining the spherical Ag nano-particle from the reaction solution by repeatedly performing centrifugation of the reaction solution two times or more,
   wherein at least one of the first and second reactions is performed in a state in which the reaction solution is not stirred.

9. A method of preparing a spherical Ag nano-particle, the method comprising:
   performing a first reaction of a reaction solution containing 10 to 20 wt % of an Ag precursor and oleylamine at a set first temperature $T_1$ in an air atmosphere;
   performing a second reaction of the reaction solution at a second temperature $T_2$ set so as to be higher than the first temperature in an air atmosphere;
   cooling the reaction solution to room temperature after the performing of the second reaction; and obtaining the spherical Ag nano-particle from the reaction solution by repeatedly performing centrifugation of the reaction solution two times or more, wherein at least one of the first and second reactions is performed in a state in which the reaction solution is not stirred.

\* \* \* \* \*